United States Patent
Lin et al.

(10) Patent No.: US 6,410,038 B1
(45) Date of Patent: *Jun. 25, 2002

(54) WATER-IN-OIL-IN-POLAR SOLVENT EMULSIONS

(75) Inventors: Zuchen Lin; William James Schulz, Jr., both of Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/593,529

(22) Filed: Jun. 14, 2000

(51) Int. Cl.⁷ .......................... A01N 25/34; A61K 7/06; A61K 7/11
(52) U.S. Cl. .................... 424/402; 424/70.12
(58) Field of Search .............. 424/402, 70.12, 424/401

(56) References Cited

U.S. PATENT DOCUMENTS

| | | | |
|---|---|---|---|
| 5,811,487 A | 9/1998 | Schulz, Jr. et al. | 524/862 |
| 5,889,108 A | 3/1999 | Zhang | 524/862 |
| 5,948,855 A * | 9/1999 | Lin et al. | 424/402 |
| 5,969,035 A | 10/1999 | Meinhardt et al. | 524/731 |

FOREIGN PATENT DOCUMENTS

EP   0958856 A1   11/1999   ......... B01F/17/00

* cited by examiner

*Primary Examiner*—Alton Pryor
(74) *Attorney, Agent, or Firm*—Charles R. Richard; James L. De Cesare

(57) ABSTRACT

Water-in-oil-in-non-aqueous polar solvent W/O/PS type multiple emulsion contains a water phase W dispersed in an oil O as the first continuous phase of a primary emulsions W/O by an emulsifier. Primary emulsion W/O is dispersed in a second continuous non-aqueous polar solvent phase PS to form multiple emulsion W/O/PS. The emulsifier is a silicone elastomer containing polyether groups which is a network of polymeric molecules crosslinked with an $\alpha,\omega$-unsaturated hydrocarbon.

16 Claims, No Drawings

WATER-IN-OIL-IN-POLAR SOLVENT EMULSIONS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

This invention is directed to water-in-oil-in-polar solvent multiple emulsions W/O/PS in which the polar solvent (PS) is a non-aqueous polar solvent(s).

BACKGROUND OF THE INVENTION

Multiple emulsions containing silicone compositions are known in the art. For example, U.S. Pat. No. 5,948,855 (Sep. 7, 1999), assigned to the assignee of this invention, discloses certain water-in-oil-in-water ($W_1/O/W_2$) type multiple emulsions. In copending application U.S. Ser. No. 09/352, 006, filed Jul. 12, 1999, assigned to the assignee of this invention, certain oil and water in oil three phase emulsions are described. In copending application U.S. Ser. No. 09/435,561, filed Nov. 8, 1999, and U.S. Ser. No. 09/498, 714, filed Feb. 7, 2000, both assigned to the assignee of this invention, certain polar solvent-in-oil-in-water ($PS_1/O/W$) type multiple emulsions, as well as certain polar solvent-in-oil-in-polar solvent ($PS_1/O/PS_2$) type multiple emulsions, are described.

However, none of the common assignee's prior references disclose a water-in-oil-in-polar solvent (W/O/PS) type multiple emulsion containing a silicone composition, which is the subject matter of the present invention. One advantage offered by a multiple emulsion of the type W/O/PS is that it can be used to isolate active ingredients which are soluble in similar phases from one another. This is particularly applicable when one active ingredient is very soluble in water W, but only marginally soluble in the non-aqueous polar solvent PS, while the other active ingredient is very soluble in PS and marginally soluble in W. Benefits can be most easily attained, however, when the active ingredients are basically insoluble in the oil O, in order to minimize their transport through O.

BRIEF SUMMARY OF THE INVENTION

The invention relates to a water-in-oil-in-non-aqueous polar solvent W/O/PS type multiple emulsion containing a water phase W dispersed in an oil O as the first continuous phase of primary emulsion W/O by an emulsifier. Primary emulsion W/O is dispersed in a second continuous non-aqueous polar solvent phase PS to form multiple emulsion W/O/PS.

The emulsifier is (i) a silicone elastomer containing polyether groups which is a network of polymeric molecules crosslinked with an $\alpha,\omega$-unsaturated hydrocarbon; (ii) a silicone elastomer containing acrylate/methacrylate grafted polyether groups which is a network of polymeric molecules crosslinked with an $\alpha,\omega$-unsaturated hydrocarbon; or (iii) a silicone elastomer containing polyether groups and alkyl groups with at least ten carbon atoms which is a network of polymeric molecules crosslinked with an $\alpha,\omega$-unsaturated hydrocarbon. In these emulsifiers, the silicone elastomer contains the continuous oil phase O, preferably a silicone oil, although it may contain other types of oils.

These and other features of the invention will become apparent from a consideration of the detailed description.

BRIEF DESCRIPTION OF THE SEVERAL VIEWS OF THE DRAWING

Not applicable.

DETAILED DESCRIPTION OF THE INVENTION

As noted above, emulsifier (i) for preparing multiple emulsions according to this invention is a silicone elastomer containing polyether groups which is a network of polymeric molecules crosslinked with an $\alpha,\omega$-unsaturated hydrocarbon. Methods for preparing this type of silicone elastomer are described in detail in the common assignee's U.S. Pat. No. 5,811,487 (Sep. 22, 1998), incorporated herein by reference.

Generally, such silicone elastomers are prepared by reacting (A) an $\equiv$Si—H containing polysiloxane; (B) a mono-alkenyl polyether; (C) an $\alpha,\omega$-unsaturated hydrocarbon such as an $\alpha,\omega$-diene, $\alpha,\omega$-diyne, or an $\alpha,\omega$-ene-yne, in the presence of (D) an oil and (E) a platinum catalyst, until a silicone elastomer is formed by crosslinking and addition of $\equiv$SiH across double or triple bonds in the $\alpha,\omega$-unsaturated hydrocarbon (C).

Emulsifier (ii) for preparing multiple emulsions according to this invention is a silicone elastomer containing acrylate/methacrylate grafted polyether groups which is a network of polymeric molecules crosslinked with an $\alpha,\omega$-unsaturated hydrocarbon. Methods for preparing this type of silicone elastomer are described in detail in the common assignee's U.S. Pat. No. 5,969,035 (Oct. 19, 1999), incorporated herein by reference.

Generally, such silicone elastomers are prepared by reacting (A) an $\equiv$Si—H containing polysiloxane; (B) a monoacrylate or monomethacrylate functionalized polyether; (C) an $\alpha,\omega$-unsaturated hydrocarbon such as an $\alpha,\omega$-diene, $\alpha,\omega$-diyne, or an $\alpha,\omega$-ene-yne, in the presence of (D) an oil and (E) a platinum catalyst, until a silicone elastomer is formed by crosslinking and addition of $\equiv$SiH across double or triple bonds in the $\alpha,\omega$-unsaturated hydrocarbon (C).

Emulsifier (iii) for preparing multiple emulsions according to this invention is a silicone elastomer containing polyether groups and alkyl groups with at least ten carbon atoms which is network of polymeric molecules crosslinked with an $\alpha,\omega$-unsaturated hydrocarbon. Methods for preparing this type of silicone elastomer are described in detail in the common assignee's copending application U.S. Ser. No. 09/352,006, filed Jul. 12, 1999, referred to above, and incorporated herein by reference.

Generally, such silicone elastomers are prepared by combining and reacting (A) an $\equiv$Si—H containing polysiloxane; (B) a mono-alkenyl polyether; (C) an $\alpha$-olefin containing at least ten carbon atoms; (D) an $\alpha,\omega$-unsaturated hydrocarbon such as an $\alpha,\omega$-diene, $\alpha,\omega$-diyne, or an $\alpha,\omega$-ene-yne, in the presence of (E) an oil, and (F) a platinum catalyst, until a silicone elastomer is formed by crosslinking and addition of $\equiv$SiH across double or triple bonds in the $\alpha,\omega$-unsaturated hydrocarbon (D).

The α,ω-unsaturated hydrocarbon can be an α,ω-diene of the formula $CH_2=CH(CH_2)_dCH=CH_2$ where d is 1–20. Some representative examples of suitable α,ω-dienes are 1,4-pentadiene; 1,5-hexadiene; 1,6-heptadiene; 1,7-octadiene; 1,8-nonadiene; 1,9-decadiene; 1,11-dodecadiene; 1,13-tetradecadiene; and 1,19-eicosadiene. Other α,ω-unsaturated hydrocarbons which can be used include α,ω-diynes of the formula $CH\equiv C(CH_2)_eC\equiv CH$; or α,ω-ene-ynes of the formula $CH_2=CH(CH_2)_eC\equiv CH$ where e is 0–20. Some representative examples of suitable α,ω-diynes are 1,3-butadiyne $HC\equiv C-C\equiv CH$ and 1,5-hexadiyne (dipropargyl) $HC\equiv C-CH_2CH_2-C\equiv CH$. One example of a suitable α,ω-ene-yne is hexene-5-yne-1 $CH_2=CHCH_2CH_2C\equiv CH$.

The common assignee's U.S. Pat. Nos. 5,811,487 and 5,889,108 contain extensive lists of appropriate oils which can be used, among which are for example, (i) volatile polydimethylsiloxanes such as hexamethyldisiloxane, octamethyltrisiloxane, and decamethylcyclopentasiloxane, (ii) nonvolatile polydimethylsiloxanes having a viscosity generally in the range of 5–1,000 centistoke ($mm^2/s$), (iii) fragrances such as musk and myrrh, and mixtures thereof.

Organic oils such as natural oils derived from animal, vegetable, or mineral sources are also suitable. Most preferred are modern cosmetic oils known to be safe for cosmetic purposes such as almond oil, apricot kernel oil, avocado oil, cacao butter (theobroma oil), carrot seed oil, castor oil, citrus seed oil, coconut oil, corn oil, cottonseed oil, cucumber oil, egg oil, jojoba oil, lanolin oil, linseed oil, mineral oil, mink oil, olive oil, palm kernel oil, peach kernel oil, peanut oil, rapeseed oil, safflower oil, sesame oil, shark liver oil, soybean oil, sunflower seed oil, sweet almond oil, tallow (beef) oil, tallow (mutton) oil, turtle oil, vegetable oil, whale oil, and wheat germ oil.

While the term non-aqueous polar solvent is intended to include solvents generally, when the multiple emulsion is intended for personal care applications, then the non-aqueous polar solvent should be one recognized as being cosmetically acceptable. Representative cosmetically acceptable non-aqueous polar solvents which can be used are monohydroxy alcohols such as ethyl alcohol and isopropyl alcohol; diols and triols such as propylene glycol, 1,2-hexanediol $CH_3(CH_2)_3CH(OH)CH_2OH$, and glycerol; glycerol esters such as glyceryl triacetate (triacetin), glyceryl tripropionate (tripropionin), and glyceryl tributyrate (tributyrin); and polyglycols such as polyethylene glycol. In applications other than personal care, these and other non-aqueous polar solvents can be employed.

The non-aqueous polar solvent, as well as the water phase, may contain a non-aqueous polar solvent soluble or water soluble active ingredient, respectively, and the oil phase may contain an oil soluble active ingredient.

Some representative non-aqueous polar solvent soluble active ingredients are (i) non-aqueous polar solvent soluble Vitamins, (ii) non-aqueous polar solvent soluble drugs including activated antiperspirant salts such as aluminum chlorohydrate and aluminum-zirconium trichlorohydrate, or (iii) α-hydroxy acids such as glycolic acid, lactic acid, tartaric acid, and citric acid, i.e., fruit acids.

The common assignee's U.S. Pat. No. 5,948,855 contains an extensive list of non-aqueous polar solvent soluble and water soluble Vitamins, and non-aqueous polar solvent soluble and water soluble drugs which can be used, among which are Vitamin C, Vitamin $B_1$, Vitamin $B_2$, Vitamin $B_6$, Vitamin $B_{12}$, niacin, folic acid, biotin, and pantothenic acid. The non-aqueous polar solvent soluble and water soluble vitamin can be used in the multiple emulsion in amounts of from 0.01–50 percent by weight.

The common assignee's U.S. Pat. No. 5,948,855 also contains an extensive list of oil soluble active ingredients such as vitamins and drugs which can be used in the multiple emulsion, among which are Vitamin $A_1$, RETINOL, $C_2$–$C_{18}$ esters of RETINOL, Vitamin E, TOCOPHEROL, esters of Vitamin E, RETINYL ACETATE, RETINYL PALMITATE, RETINYL PROPIONATE, α-TOCOPHEROL, TOCOPHERSOLAN, TOCOPHERYL ACETATE, TOCOPHERYL LINOLEATE, TOCOPHERYL NICOTINATE, TOCOPHERYL SUCCINATE, and mixtures thereof. The oil-soluble vitamin or drug can be used in the multiple emulsion in amounts of from 0.01–50 percent by weight.

W/O/PS multiple emulsions according to the invention can be prepared by forming a primary emulsion W/O and combining it with a non-aqueous polar solvent PS. For the primary emulsion W/O, it is preferred to use 0.01–99.99 percent by weight of water including the weight of any water soluble active ingredient such as a vitamin which may be carried therein. The oil phase O of the primary emulsion W/o can also comprise 0.01–99.99 percent by weight including the weight of silicone elastomer, oil, and any oil soluble vitamin or active ingredient which may be carried therein. Preferably, the water phase comprises 20–95 percent by weight of the primary emulsion W/O and the oil phase comprises 15–80 percent by weight of the primary emulsion W/O. Multiple emulsions W/O/PS can then be prepared simply by mixing together 0.1–80 percent by weight of primary emulsion W/O and 20–99.9 percent by weight of a non-aqueous polar solvent PS.

EXAMPLES

The following examples are set forth in order to illustrate this invention in more detail.

Example 1

Preparation of Primary Emulsion W/O 20.8 g of a solution containing 20 percent by weight of a silicone elastomer containing polyether groups in decamethylcyclopentasiloxane, prepared according to the method described in U.S. Pat. No. 5,811,487, in which about 9 percent of the repeating units in the backbone are units containing the moiety —$(CH_2CH_2O)_n$— in which n is 12, were weighed into a glass beaker, and mixed at 800 rpm (84 rad/s) using a mechanical mixer. Over a 5 minute period, 22.9 g of de-ionized water was added to the beaker and mixed, to form a primary emulsion W/O. In forming the primary emulsion W/O, the silicone elastomer was an emulsifier for water, and the phase O was the silicone elastomer and decamethylcyclopentasiloxane.

Example 2

Preparation of Multiple Emulsion W/O/Ps$_1$ 26.0 g of a solution containing one percent by weight of carbomer thickener in propylene glycol (PS$_1$) was weighted into a glass beaker and mixed at 800 rpm (84 rad/s) using a mechanical mixer. Carbomer is a crosslinked polyacrylic acid polymer sold under the tradename CARBOPOL EDT 2001, by B. F. Goodrich Company, Brecksville, Ohio. 12.0 g of the primary emulsion W/O prepared in Example 1 was added to the beaker and mixed at 1000 rpm (104 rad/s) for 20 minutes. The product was a turbid multiple emulsion that was stable. Examination of the product by optical microscopy confirmed it as multiple emulsion W/O/PS$_1$.

Example 3
Preparation of Multiple Emulsion W/O/PS$_2$ 22.7 g of a solution containing 3.2 percent by weight of carbomer thickener in 1,2-hexanediol (PS$_2$) was weighted into a glass beaker and mixed at 800 rpm (84 rad/s) using a mechanical mixer. 10.7 g of the primary emulsion W/O prepared in Example 1 was added to the beaker and mixed at 1000 rpm (104 rad/s) for 20 minutes. The product was a turbid multiple emulsion that was stable. Examination of the product by optical microscopy confirmed it as multiple emulsion W/O/PS$_2$.

The W/O/PS multiple emulsion is useful in personal care, for example, in preparing antiperspirants and deodorants. It can be used in skin creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers. It can be used in hair shampoos, hair conditioners, hair sprays, mousses, permanents, depilatories, and cuticle coats. In cosmetics, it can be added to make-ups, color cosmetics, foundations, blushes, lipsticks, eyeliners, mascara, oil removers, color cosmetic removers, and powders. In such applications, it may include oil soluble, polar solvent soluble, and water soluble ingredients such as vitamins as noted above.

The W/O/PS multiple emulsion is also capable of functioning as a carrier for pharmaceuticals, biocides, herbicides, pesticides, and other biologically active substances; and it has utility as an additive for cellulosic or synthetic non-woven carrier substrates used in wet-like cleansing wipes such as wet-wipes, tissues, and towels, marketed generally for personal hygiene and household cleaning tasks.

While the most preferred silicone elastomers for use according to this invention are described in common assignee's U.S. Pat. Nos. 5,811,487; 5,969,035; and copending application U.S. Ser. No. 09/352,006, filed Jul. 12, 1999; other silicone elastomers containing polyether groups may be substituted, including silicone elastomers containing polyether groups and higher alkyl groups, provided the performance and benefits are equivalent. Reference may be had, for example, to common assignee's U.S. Pat. No. 5,889,108 (Mar. 30, 1999) and U.S. Pat. No. 5,948,855 (Sep. 7, 1999) for other silicone elastomers considered equivalent.

Variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. A composition comprising a water-in-oil-in-non-aqueous polar solvent W/O/PS multiple emulsion including a water phase W dispersed in an oil O first continuous phase of primary emulsion W/O by an emulsifier, the primary emulsion W/O being dispersed in a second continuous non-aqueous polar solvent phase PS to form multiple emulsion W/O/PS, the emulsifier being a silicone elastomer containing polyether groups which is a network of crosslinked polymeric molecules.

2. A composition according to claim 1 in which the emulsifier is a silicone elastomer containing acrylate/methacrylate grafted polyether groups which is a network of crosslinked polymeric molecules, or a silicone elastomer containing polyether groups and alkyl groups with at least ten carbon atoms which is a network of crosslinked polymeric molecules.

3. A composition according to claim 1 in which the non-aqueous polar solvent is a monohydroxy alcohol, a diol, a triol, a glycerol ester, or a polyglycol.

4. A composition according to claim 1 in which the oil is (i) a volatile polydimethylsiloxane, (ii) a nonvolatile polydimethylsiloxane with a viscosity of 5–1,000 centistoke (mm$^2$/s), (iii) a fragrance, (iv) a natural organic oil derived from an animal, vegetable, or mineral source, or (v) a mixture of oils (i)–(iv).

5. A composition according to claim 1 in which the non-aqueous polar solvent contains a non-aqueous polar solvent soluble active ingredient selected from the group consisting of vitamins, activated antiperspirant salts, drugs, and α-hydroxy acids; the oil phase contains an oil soluble active ingredient selected from the group consisting of vitamins and drugs; and the water phase contains a water soluble active ingredient selected from the group consisting of vitamins, activated antiperspirant salts, drugs, and α-hydroxy acids.

6. A composition according to claim 1 in which the water phase comprises 20–95 percent by weight of the primary emulsion W/O, the oil phase comprises 15–80 percent by weight of the primary emulsion W/O, and the multiple emulsion W/O/PS comprises 0.1–80 percent by weight of primary emulsion W/O and 20–99.9 percent by weight of the non-aqueous polar solvent PS.

7. A product containing the composition according to claim 1, the product being selected from the group consisting of antiperspirants, deodorants, skin creams, skin care lotions, moisturizers, facial treatments, acne removers, wrinkle removers, personal cleansers, facial cleansers, bath oils, perfumes, colognes, sachets, sunscreens, pre-shave lotions, after-shave lotions, shaving soaps, shaving lathers, hair shampoos, hair conditioners, hair sprays, mousses, permanents, depilatories, cuticle coats, make-up, color cosmetics, foundations, blushes, lipsticks, eyeliners, mascara, oil removers, color cosmetic removers, bath powders, body powders, pharmaceuticals, biocides, herbicides, pesticides, biologically active substances, cellulosic substrates, synthetic nonwoven substrates, wet-cleansing wipes, tissues, and towels.

8. A method of treating hair, skin, or underarm, comprising applying to hair, skin, or underarm the composition according to claim 1.

9. A composition comprising a water-in-oil-in-non-aqueous polar solvent W/O/PS multiple emulsion including a water phase W dispersed in an oil O first continuous phase of primary emulsion W/O by an emulsifier, the primary emulsion W/O being dispersed in a second continuous non-aqueous polar solvent phase PS to form multiple emulsion W/O/PS, the emulsifier being a silicone elastomer containing polyether groups which is a network of polymeric molecules crosslinked with an α,ω-unsaturated hydrocarbon.

10. A composition according to claim 9 in which the emulsifier is a silicone elastomer containing acrylate/methacrylate grafted polyether groups which is a network of polymeric molecules crosslinked with an α,ω-unsaturated hydrocarbon, or a silicone elastomer containing polyether groups and alkyl groups with at least ten carbon atoms which is a network of polymeric molecules crosslinked with an α,ω-unsaturated hydrocarbon.

11. A composition according to claim 9 in which the non-aqueous polar solvent is a monohydroxy alcohol, a diol, a triol, a glycerol ester, or a polyglycol.

12. A composition according to claim 9 in which the oil is (i) a volatile polydimethylsiloxane, (ii) a nonvolatile polydimethylsiloxane with a viscosity of 5–1,000 centistoke (mm$^2$/s), (iii) a fragrance, (iv) a natural organic oil derived from an animal, vegetable, or mineral source, or (v) a mixture of oils (i)–(iv).

13. A composition according to claim 9 in which the non-aqueous polar solvent contains a non-aqueous polar solvent soluble active ingredient selected from the group consisting of vitamins, activated antiperspirant salts, drugs, and α-hydroxy acids; the oil phase contains an oil soluble active ingredient selected from the group consisting of vitamins and drugs; and the water phase contains a water soluble active ingredient selected from the group consisting of vitamins, activated antiperspirant salts, drugs, and α-hydroxy acids.

14. A composition according to claim 9 in which the water phase comprises 20–95 percent by weight of the primary emulsion W/O, the oil phase comprises 15–80 percent by weight of the primary emulsion W/O, and the multiple emulsion W/O/PS comprises 0.1–80 percent by weight of primary emulsion W/O and 20–99.9 percent by weight of the non-aqueous polar solvent PS.

15. A product containing the composition according to claim 9, the product being selected from the group consisting of antiperspirants, deodorants, skin creams, skin care lotions, moisturizers, facial treatments, acne removers, wrinkle removers, personal cleansers, facial cleansers, bath oils, perfumes, colognes, sachets, sunscreens, pre-shave lotions, after-shave lotions, shaving soaps, shaving lathers, hair shampoos, hair conditioners, hair sprays, mousses, permanents, depilatories, cuticle coats, make-up, color cosmetics, foundations, blushes, lipsticks, eyeliners, mascara, oil removers, color cosmetic removers, bath powders, body powders, pharmaceuticals, biocides, herbicides, pesticides, biologically active substances, cellulosic substrates, synthetic nonwoven substrates, wet-cleansing wipes, tissues, and towels.

16. A method of treating hair, skin, or underarm, comprising applying to hair, skin, or underarm the composition according to claim 9.

* * * * *